US006855121B1

(12) United States Patent
Chan et al.

(10) Patent No.: US 6,855,121 B1
(45) Date of Patent: Feb. 15, 2005

(54) BLOOD-RELATED DIALYSIS AND TREATMENT

(75) Inventors: Grace Sze Man Chan, Penshurst (AU); Ellie Faramus, New Beach (AU); Jason Ian Kien Huat Lee, Beecroft (AU); Chenicheri Hariharan Nair, Castle Hill (AU); Philip John Roeth, Castle Hill (AU)

(73) Assignee: Gradipore Limited, Frenchs Forest (AU)

( * ) Notice: Subject to any disclaimer, the term of this patent is extended or adjusted under 35 U.S.C. 154(b) by 0 days.

(21) Appl. No.: 09/470,822

(22) Filed: Dec. 23, 1999

(30) Foreign Application Priority Data

Dec. 23, 1998 (AU) ............................................. PP7908

(51) Int. Cl.$^7$ ........................ A61M 37/00; B01D 63/00; C02F 1/44; C02F 1/40; C25B 7/00
(52) U.S. Cl. ..................... 604/6.08; 604/5.01; 204/518; 204/520; 204/543; 204/627; 210/748; 210/195.2; 210/321.71; 210/500.21; 210/767
(58) Field of Search ............................ 422/44–48, 101; 604/4.01, 6.01, 5.01–5.04, 6.04, 6.09, 6.11, 6.16, 28, 29, 6.08; 128/898; 210/645–47, 650–52, 748, 767, 790–93, 194, 195.2, 196, 222, 223, 321.6, 321.71–321.72, 321.75, 321.84, 322, 323.1, 902, 903, 905, 500.1–500.21; 204/155–56, 450, 518, 520, 543, 627

(56) References Cited

U.S. PATENT DOCUMENTS

| | | | |
|---|---|---|---|
| 3,878,564 A | 4/1975 | Yao et al. | |
| 4,036,748 A | 7/1977 | Knickel et al. | |
| 4,043,895 A | 8/1977 | Gritzner | |
| 4,045,337 A | 8/1977 | Knickel et al. | |
| 4,045,455 A | 8/1977 | Vogel | |
| 4,069,215 A | 1/1978 | Elfert et al. | |
| 4,115,225 A | 9/1978 | Parsi | |
| 4,123,342 A | 10/1978 | Ahlgren | |
| 4,174,439 A | 11/1979 | Rauenbusch et al. | |
| 4,196,304 A | 4/1980 | Naumann | |
| 4,204,929 A | 5/1980 | Bier | |
| 4,217,227 A | 8/1980 | Elfert et al. | |
| 4,238,306 A | 12/1980 | Perry et al. | |
| 4,238,307 A | 12/1980 | Perry et al. | |

(List continued on next page.)

FOREIGN PATENT DOCUMENTS

| | | |
|---|---|---|
| AU | 88/07406 | 10/1988 |
| WO | WO 97/14486 | 4/1997 |
| WO | WO 98/21384 | 5/1998 |
| WO | WO 98/43718 | 10/1998 |

*Primary Examiner*—Patricia Bianco
(74) *Attorney, Agent, or Firm*—Baker & McKenzie

(57) ABSTRACT

A method of treating blood or plasma of a subject to remove metabolic contaminants by electrophoresis. Blood or plasma from the subject is placed in a first solvent stream, the first solvent stream being separated form a second solvent stream by an electrophoretic membrane. Applying an electric potential between the two solvent streams causes movement of metabolic contaminants from the blood or plasma through the membrane into the second solvent stream while cellular and biomolecular components of the blood or plasma are substantially retained in the first sample stream, or if entering the membrane, being substantially prevented from entering the second solvent stream. Optionally, periodically stopping and reversing the electric potential causes movement of any cellular and biomolecular components of the blood or plasma having entered the membrane to move back into the first solvent stream, wherein substantially not causing any metabolic contaminants that have entered the second solvent stream to re-enter first solvent stream. The potential is maintained until the desired amount of removal of the metabolic contaminants from the blood or plasma in the first solvent stream is achieved. The treated blood or plasma in the first solvent stream is returned to the subject.

42 Claims, 10 Drawing Sheets

U.S. PATENT DOCUMENTS

| | | | |
|---|---|---|---|
| 4,252,652 A | 2/1981 | Elfert et al. |
| 4,259,079 A | 3/1981 | Blum |
| 4,269,967 A | 5/1981 | Elfert et al. |
| 4,276,140 A | 6/1981 | Jain |
| 4,279,724 A | 7/1981 | Hearn et al. |
| 4,299,677 A | 11/1981 | Venkatasubramanian et al. |
| 4,322,275 A | 3/1982 | Jain |
| 4,362,612 A | 12/1982 | Bier |
| 4,376,023 A | 3/1983 | Venkatsubramanian et al. |
| 4,381,232 A | 4/1983 | Brown |
| 4,383,923 A | 5/1983 | Elfert |
| 4,396,477 A | 8/1983 | Jain |
| 4,441,978 A | 4/1984 | Jain |
| 4,461,693 A | 7/1984 | Jain |
| 4,533,447 A | 8/1985 | Meldon |
| 4,608,140 A | 8/1986 | Goldstein |
| 4,661,224 A | 4/1987 | Goldstein et al. |
| 4,673,483 A | 6/1987 | Mandle |
| 4,711,722 A | 12/1987 | Toyoshi et al. |
| 4,746,647 A | 5/1988 | Svenson |
| 4,780,411 A | 10/1988 | Piejko et al. |
| 4,897,169 A | 1/1990 | Bier et al. |
| 4,963,236 A | 10/1990 | Rodkey et al. |
| 5,043,048 A | 8/1991 | Muralidhara |
| 5,080,770 A | 1/1992 | Culkin |
| 5,082,548 A | 1/1992 | Faupel et al. |
| 5,087,338 A | 2/1992 | Perry et al. |
| 5,096,547 A | 3/1992 | Klotz et al. |
| 5,114,555 A | 5/1992 | Stimpson |
| 5,127,999 A | 7/1992 | Klotz et al. |
| 5,160,594 A | 11/1992 | Huff et al. |
| 5,173,164 A | 12/1992 | Egen et al. |
| 5,185,086 A | 2/1993 | Kaali et al. |
| 5,238,570 A | 8/1993 | Hugl et al. |
| 5,277,774 A | 1/1994 | Shmidt et al. |
| 5,336,387 A | 8/1994 | Egen et al. |
| 5,340,449 A | 8/1994 | Shukla |
| 5,352,343 A | 10/1994 | Bailes et al. |
| 5,407,553 A | 4/1995 | Herron et al. |
| 5,420,047 A | 5/1995 | Brandt et al. |
| 5,437,774 A * | 8/1995 | Laustsen .................... 204/518 |
| 5,441,646 A | 8/1995 | Heller et al. |
| 5,490,939 A | 2/1996 | Gerigk et al. |
| 5,503,744 A | 4/1996 | Ikematsu et al. |
| 5,504,239 A | 4/1996 | Mehl et al. |
| 5,558,753 A | 9/1996 | Gallagher et al. |
| 5,561,115 A | 10/1996 | Tenold |
| 5,565,102 A | 10/1996 | Brandt et al. |
| 5,610,285 A | 3/1997 | Lebing et al. |
| 5,650,055 A * | 7/1997 | Margolis .................... 204/518 |
| 5,662,813 A | 9/1997 | Sammons et al. |
| 5,723,031 A | 3/1998 | Durr et al. |
| 5,733,442 A | 3/1998 | Shukla |
| 5,736,023 A | 4/1998 | Gallagher et al. |
| 5,804,684 A * | 9/1998 | Su ........................... 536/25.4 |
| 5,868,938 A | 2/1999 | Bomer et al. |
| 5,891,736 A | 4/1999 | Chapoteau et al. |
| 5,906,724 A | 5/1999 | Sammons et al. |
| 5,938,904 A | 8/1999 | Bader et al. |
| 5,986,075 A | 11/1999 | DuBose et al. |
| 6,093,296 A | 7/2000 | Soane et al. |
| 6,117,297 A | 9/2000 | Goldstein |
| 6,129,842 A | 10/2000 | Kostanian |
| 6,171,825 B1 | 1/2001 | Chan et al. |

\* cited by examiner

BLOOD-RELATED DIALYSIS AND TREATMENT

TECHNICAL FIELD

The present invention relates to methods suitable for treating or processing blood or plasma to remove or reduce the concentration of unwanted components, and particularly dialysis methods applicable to renal dialysis.

BACKGROUND ART

In healthy individuals, the kidney functions to remove excess water, salts and small proteins from the blood circulation. Nitrogenous wastes removed by the kidney include urea, the final metabolic destiny of excess dietary nitrogen, creatinine which is produced during muscle activity, and uric acid, an endpoint product of nucleotide metabolism. Current renal dialysis technology relies on equilibrium/diffusion principles and transmembrane pressure to remove nitrogenous wastes, salts and excess water from the bloodstream of patients experiencing chronic or acute renal failure. This requires two to three hours of dialysis treatment on three or four occasions each week. There are significant deficiencies in existing dialysis technologies, including suboptimal biocompatibility of the dialysis membranes used, the inadequacy of existing technology in the removal of some solutes, such as phosphates, and poor removal of low molecular weight proteins such as beta-2 microglobulin. GradiFlow™ technology, or a modification thereof, can be used to perform blood dialysis for purposes of renal replacement therapy, such that these deficiencies in conventional dialysis could be addressed. These deficiencies can be addressed by including the application of an electrical potential through a blood dialysis chamber to accelerate the removal of charged solutes such as phosphate ions and proteins, as well as charged nitrogenous wastes and other salt ions such as sodium, potassium, chloride and so on. The demonstrated protein separation capacity of the GradiFlow™ technology can be applied to the removal of specific proteins from the blood or plasma circulations, with the intention of treating disease symptoms mediated by those proteins. Examples of such disease states include rheumatoid arthritis and a host of other autoantibody mediated autoimmune diseases, which could be treated by the selective removal of autoantibody or other disease related proteins from the patients blood circulation.

The present inventors have developed a device based on GradiFlow™ technology (AU 601040) which can be used to selectively remove solutes, metabolites and proteins from either blood or plasma. Such a device can be used as either an add-on module to existing dialysis machines, or as a stand-alone device used to filter the blood of dialysis patients as a specific therapeutic measure to remove metabolites and proteins after conventional dialysis therapy has already been applied.

One of the key advantages of the GradiFlow™ is its capacity to desalt. In the present system, this is achieved by the retention of the desired macromolecule in a chamber sandwiched between two restriction membranes. Essentially the GradiFlow™ can be re-configured so that dialysis of a mixture of components is possible.

Internationally, 800,000 people suffer from chronic renal failure which implies that their kidneys can never perform the way they should. In medicine, dialysis is a therapy which eliminates the toxic wastes from the body due to kidney failure. There are two types of dialysis a) haemodialysis and b) peritoneal dialysis.

Haemodialysis is usually performed in dialysis centers, where the treatment entails dialysis for 4 hours three times a week. This sharply interferes with the quality of life of patients and also their productivity to the community at large. The present technology entails the re-routing of blood from the body to a filter made of plastic capillaries. The blood is purified when the waste products diffuse from the blood across the membrane of these tiny capillaries. The blood is then return to the body via the arm. The main advantage to this system is that patient training is not required. The main disadvantages are that dialysis graft failure is common and there is lack of freedom on the part of the patient because of the requirement to report to a center for treatment.

In peritoneal dialysis, the body's own membrane is used as a filter, and the fluid drained in and out of the abdomen replaces the kidneys in getting rid of toxins. There are some great advantages to this system which include the fact that this can be done at home. The domestic use of this, however, requires careful technique and has the added disadvantage of peritonitis and membrane failure.

Gradiflow™ Technology

The Gradiflow™ is a unique preparative electrophoresis technology for macromolecule separation which utilizes tangential flow across a polyacrylamide membrane, such as a selective membrane composed of polyacrylamide hydrogel, when a charge is applied across the membrane. The general design of the Gradiflow™ system facilitates the purification of proteins and other macromolecules under near native conditions, that is under conditions in which the pressure across solvent streams is substantially equal. This results in higher yields and excellent recovery.

In essence, the Gradiflow™ technology is bundled into a cartridge comprising of three or more membranes, at least one of which is a selective membrane composed of polyacrylamide hydrogel, housed in a system of specially engineered grids and gaskets which allow separation of macromolecules by charge and/or molecular weight, while the pressure in the solvent streams are substantially equal. The system can also concentrate and desalt/dialyse at the same time. The multimodal nature of the system allows this technology to be used in a number of other areas especially in therapy for the dialysis of blood in situations like renal failure. The configuration of the Gradiflow™ apparatus containing a selective membrane composed of polyacrylamide hydrogel, and in which the pressure in the solvent streams Are substantially equal allows the possibility of producing a simple portable device which will have the dual capacity of being easy to use an concurrently producing high quality dialysis.

DISCLOSURE OF INVENTION

In a first general aspect, the present invention consists in use of GradiFlow™ in the processing of blood or plasma from a subject in order to remove or reduce the concentration of unwanted solutes and macromolecules from the blood or plasma.

In a preferred embodiment, GradiFlow™ is used in renal dialysis, either as a replacement of current dialysis methods or as a supplement to current renal dialysis.

In a second aspect, the present invention consists in a method of treating blood or plasma of a subject to remove or reduce the concentration of metabolic contaminants, the method comprising:

a) placing blood or plasma from the subject in a first solvent stream, the first solvent stream being separated from a second solvent stream by an electrophoretic membrane;

(b) applying an electric potential between the two solvent streams causing movement of metabolic contaminants from the blood or plasma through the membrane into the second solvent stream while cellular and biomolecular components of the blood or plasma are substantially retained in the sample stream, or if entering the membrane, being substantially prevented from entering the second solvent stream;

(c) optionally, periodically stopping and reversing the electric potential to cause movement of any cellular and biomolecular components of the blood or plasma having entered the membrane to move back into the first solvent stream, wherein substantially not causing any metabolic contaminants that have entered the second solvent stream to re-enter the first solvent stream;

(d) maintaining step (b), and optionally step (c) if used, until the desired amount of removal of the metabolic contaminants from the blood or plasma in the first solvent stream is achieved; and (e) returning the treated blood or plasma in the first solvent stream to the subject.

In a preferred embodiment, the subject is a renal dialysis patient.

The blood or plasma is preferably recirculated between the subject and the first solvent stream.

In a further preferred embodiment the second aspect of the invention, the electrophoretic membrane has a molecular mass cut-off close to apparent molecular mass of metabolic contaminants. It will be appreciated, however, that the membrane may have any required molecular mass cut-off depending on the application.

Preferably, the metabolic contaminants are solutes including phosphates, nitrogenous wastes like urea and uric acid, or macromolecules including beta-2 microglobulin and other unwanted proteins including autoantibodies.

Preferably, the electrophoretic membrane has a molecular mass cut-off of between about 3 and 1000 kDa. It will be appreciated, however, that other size membranes may be applicable, depending on the treatment process required. A number of different membranes may also be also used in a desired or useful configuration.

The electric potential applied during the method should preferably not substantially adversely effect the cells or proteins present in blood or plasma. An electric potential of up to about 100 volts has been found to be suitable. It will be appreciated, however, that other voltages may be used.

In a third aspect, the present invention consists in a method of renal dialysis, the method comprising carrying out haemodialysis on blood or plasma of a patient followed by subjecting the blood or plasma of the patient to the method according to the second aspect of the present invention.

As conventional haemodialysis often fails to remove certain metabolic contaminants from the blood of renal patients which can result in the build-up of these contaminants, a second treatment process using the method according to the second aspect of the present invention has the potential to selectivity remove these contaminants.

Preferably, the method comprises:

(a) carrying out haemodialysis on blood or plasma of the patient;

(b) placing blood or plasma from the haemodialysed patient in a first solvent stream, the first solvent stream being separated from a second solvent by an electrophoretic membrane;

(c) applying an electric potential between the two solvent streams causing movement of metabolic contaminants from the blood or plasma through the membrane into the second solvent stream while cellular and biomolecular components of the blood or plasma are substantially retained in the first sample stream, or if entering the membrane, being substantially prevented from entering the second solvent stream;

(d) optionally, periodically stopping and reversing the electric potential to cause movement of any cellular and biomolecular components of the blood or plasma having entered the membrane to move back into the first solvent stream, wherein substantially not causing any metabolic contaminants that have entered the second solvent stream to re-enter the first solvent stream;

(e) maintaining step (c), and optionally step (d) if used, until the desired amount of removal or reduction of the metabolic contaminants from the blood or plasma in the first solvent stream is achieved; and (f) returning the treated blood or plasma in the first solvent stream to the patient.

The contaminants can be phosphates or proteins such as beta-2 microglobulin or autoantibodies. It will be appreciated, however, that other unwanted metabolic contaminants can also be removed in this process.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood a preferred form will be described with reference to the accompanying drawings.

MODES FOR CARRYING OUT THE INVENTION

Applications
Urea Removal by Passive Diffusion
Demonstration of the Removal of Urea from Aqueous Solutions
Method One mg/mL Urea was dissolved in phosphate buffered saline (PBS) and placed in the upstream of a GradiFlow™ device. PBS buffer, chilled to 4° C. with ice, was recirculated in the buffer stream. The up and down streams were pumped through the GradiFlow™ device at 20 mL/min and samples taken from both streams at 10 minute intervals. No voltage or current was applied during this procedure. The timed samples were then assayed for urea content.

Results

Figure 1:
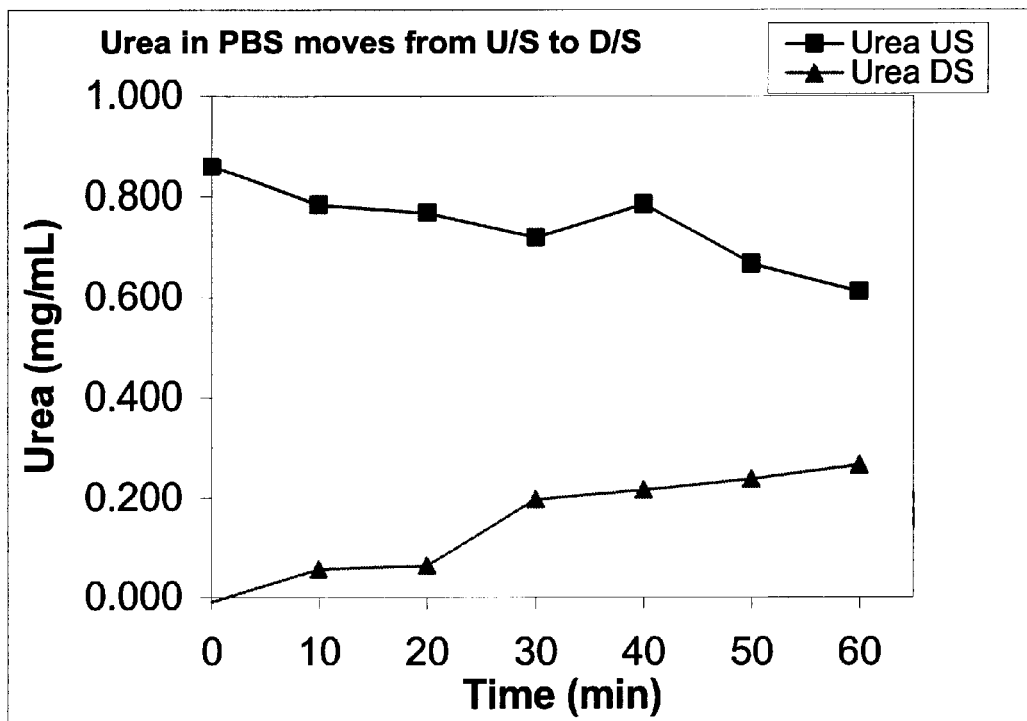
FIG. 1. Removal of Urea in PBS from upstream to downstream of GradiFlow™.

The data in FIG. 1 show the concentration of Urea in the upstream (solid squares) and in the downstream (hatched squares). The concentration of Urea in the upstream decreased over time, while the concentration of urea in the downstream increased. This result indicates that urea can be removed from aqueous solution by passive diffusion.

Removal of Urea from Plasma
Method

Unmodified human plasma, or human plasma to which 1 mg/mL Urea had been added, was placed in the upstream of a GradiFlow device. PBS buffer, chilled to 4° C. with ice, was recirculated in the buffer stream. The up and down streams were pumped through the GradiFlow device at 20 mL/min and samples taken from both streams at 10 minute intervals. No voltage or current was applied during this procedure. The timed samples were then assayed for urea content.

Results

Figure 2:
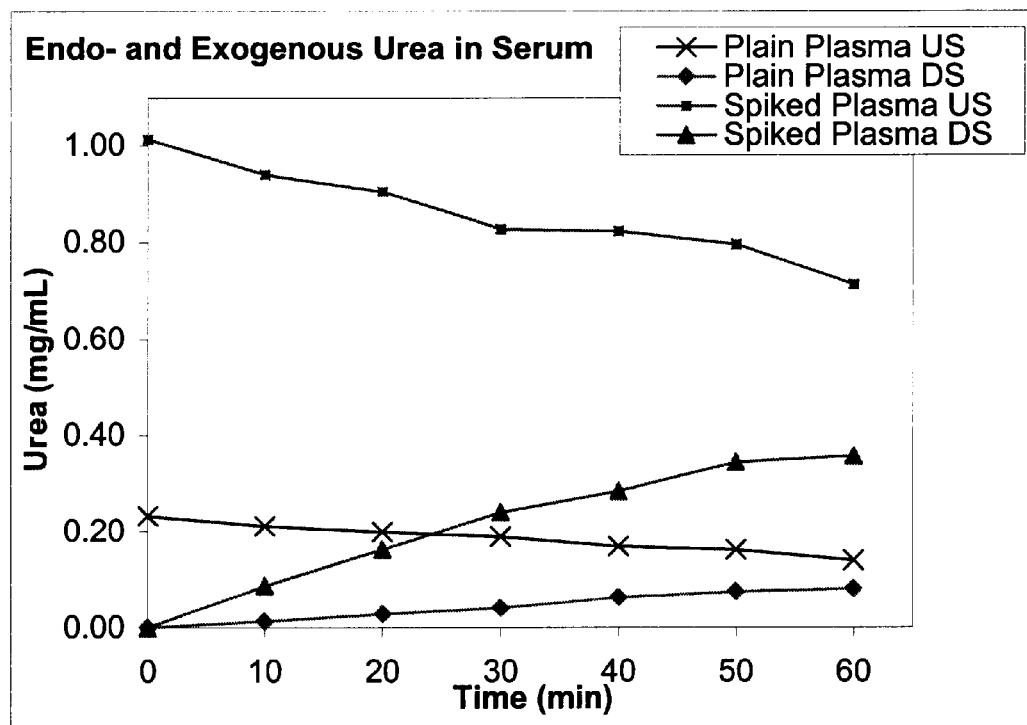
FIG. 2. Removal of endogenous and exogenous Urea from plasma by passive diffusion.

The data in FIG. 2 show the concentration of endogenous Urea in the upstream (solid diamonds) and in the downstream (hatched diamonds) when unmodified plasma was used in this experiment. The concentration of Urea in the upstream and downstream when exogenous Urea was added to the sample is shown in red squares and pink triangles respectively. As shown above for aqueous solution, the concentration of Urea in the upstream decreased over time, while the concentration of urea in the downstream increased. This result indicates that urea may be removed from plasma by passive diffusion.

Factors Affecting the Removal of Urea from Aqueous Solutions
Method

Urea was dissolved in an appropriate buffer and placed in the sample stream of a GradiFlow™ device, with the GradiFlow™ cartridge constructed in dialysis configuration. The circulating buffer stream was selected to match the solution in which Urea had been dissolved. The starting Urea concentration, buffer pH, salt concentration, temperature of the system and applied voltage/current were varied systematically to determine the effect each variable had on the rate of Urea removal. The Urea solution was pumped through the GradiFlow™ device at 20 mL/min, with samples generally being taken at 10 minute intervals. The timed samples were then assayed with urea content.

The Effect of Applied Current on Urea Removal

One mg/mL Urea was dissolved in Tris Borate buffer, pH 9.0 and processed through the GradiFlow as described above. Electrical currents from 0 to 1.5 Amps were applied to the system, however, no change in Urea removal rate was observed, indicating that the rate of Urea removal was insensitive to the applied current.

Voltage Dependence of Urea Movement

One mg/mL Urea was dissolved in Tris/Borate buffer at pH 9.0 and circulated in the sample stream of a GradiFlow™ cartridge constructed in the dialysis configuration. Various electrical potentials from 0 to 100V were applied to the GradiFlow™ system. Varying electrical results in no significant alteration to the rate of Urea removal from the sample stream.

pH Dependence of Urea Removal

One mg/mL Urea was dissolved in GABA/acetic acid buffer pH 3, Hepes/Imidazole buffer pH 6.0 and Tris/Borate buffer pH 9.0, and processed through the GradiFlow™ with an applied electrical potential of 50V. No significant in the rate of Urea removal was observed as a functional of changes in buffer pH.

The Effect of NaCl Concentration on Urea Removal

One mg/mL Urea was dissolved in 20 mM phosphate buffer containing 0 to 150 mM NaCl and processed through the GradiFlow™ in dialysis configuration using 50 kDa cutoff membranes. No electrical potential was applied in these experiments. The presence of increasing concentrations of NaCl has no effect in the diffusion of Urea in the GradiFlow™ instrument.

The Effect of Membrane Pore Size on the Removal of Urea from Aqueous Solutions

Figure 3:
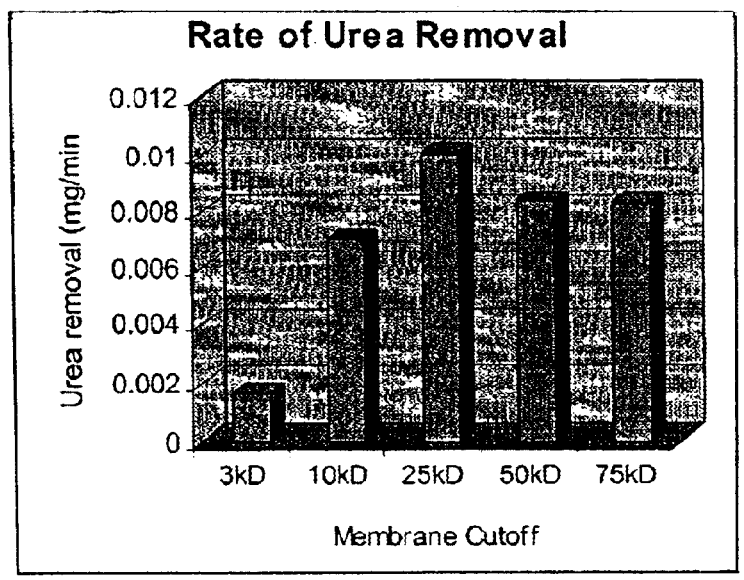
FIG. 3. The rate of Urea removal is dependent on the membrane molecular weight cutoff.

One mg/mL Urea was dissolved in PBS and processed in the GradiFlow™ using membranes with molecular weigh cutoff values between 3 and 75 kDa. Ten minute time samples were taken during these runs and the slope of these curves determined as the rate of Urea removal. FIG. 3 shows the relationship between membrane molecular weight cutoff and the rate of Urea removal from aqueous solutions.

The Effect of Temperature on the Removal of Urea

Figure 4:
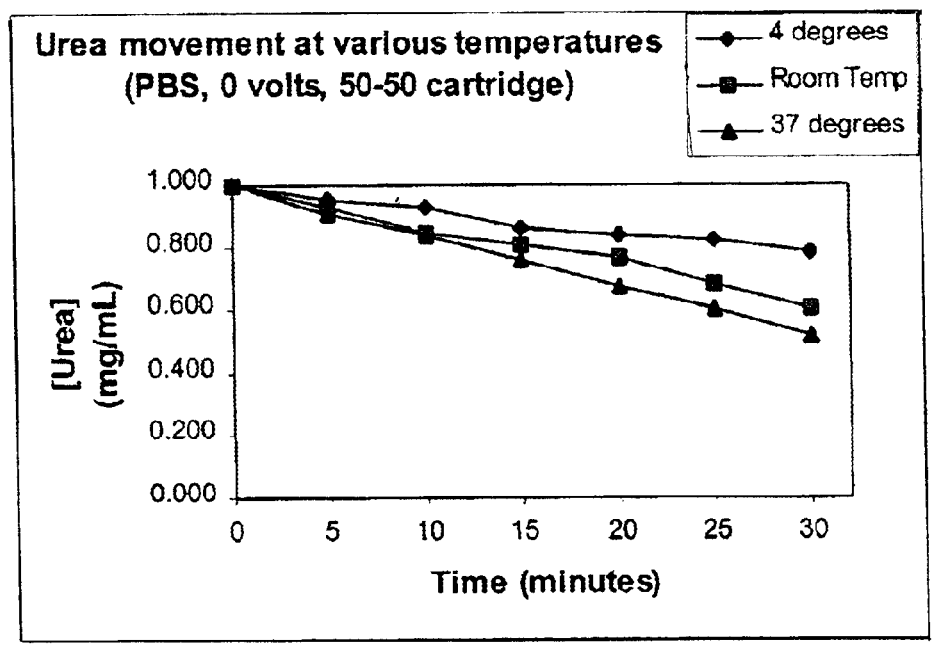
FIG. 4. Increasing temperature increases the rate of Urea removal in the GradiFlow™ device.

One mg/mL Urea was dissolved in PBS and processed in the GradiFlow™ as previously. The buffer temperature was maintained at temperatures between 4 and 37° C. and the removal of Urea determined. FIG. 4 shows that increasing buffer temperature increased the rate of Urea removal, consistent with a passive diffusion phenomenon.

The Effect of Urea Concentration of the Rate of Urea Removal

Figure 5:
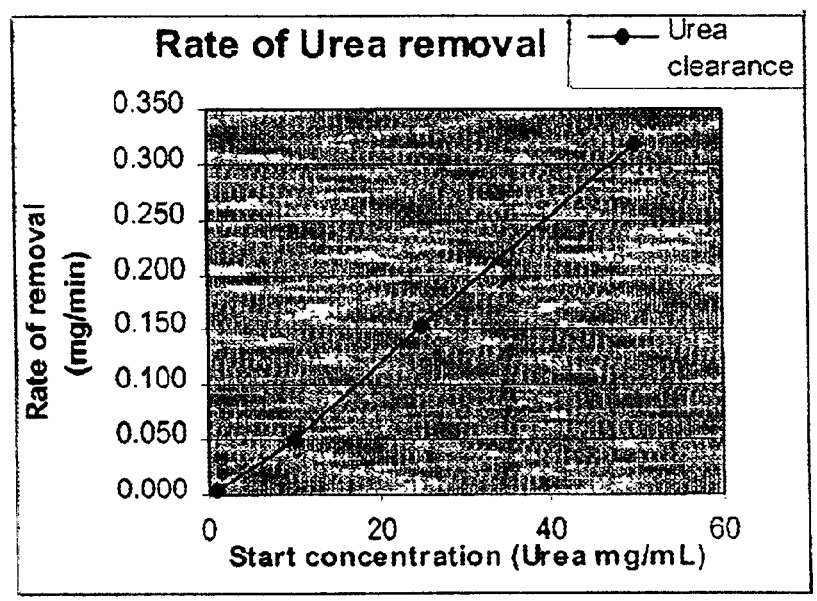
FIG. 5. The rate of Urea removal, expressed in mg Urea removed per minute, is proportional to the Urea concentration on the sample stream.

Urea at concentrations between 1 and 50 mg/mL was dissolved in PBS and processed through the GradiFlow™ as above. The rate of Urea removal was determined from time course experiments and calculated in units of urea removed per minute. FIG. 5 shows that the rate of Urea removal increases with Urea concentration, again consistent with a passive diffusion phenomenon.

Electrically Driven Creatinine Removal

Demonstration of the Migration of Creatinine

One hundred Tg/mL creatinine was dissolved in GABA/acetate buffer, pH 3, and placed in the upstream of a GradiFlow™ device, using 3 kDa restriction membranes and a 50 kDa separation membrane. GABA/acetate buffer, chilled to 4° C., was recirculated in the buffer stream. An electrical potential of 25V was applied to the stream, using reverse polarity. Samples were collected from the up down streams at 5 minutes intervals and the creatinine concentrations in these samples determined. The results obtained show that creatinine was rapidly removed from the upstream. The transient rise in the downstream creatinine concentration indicates that creatinine moved through the downstream, but was not retained by the 3 kDa membrane. Creatinine therefore passed through the restriction membrane into the buffer stream.

Figure 6:
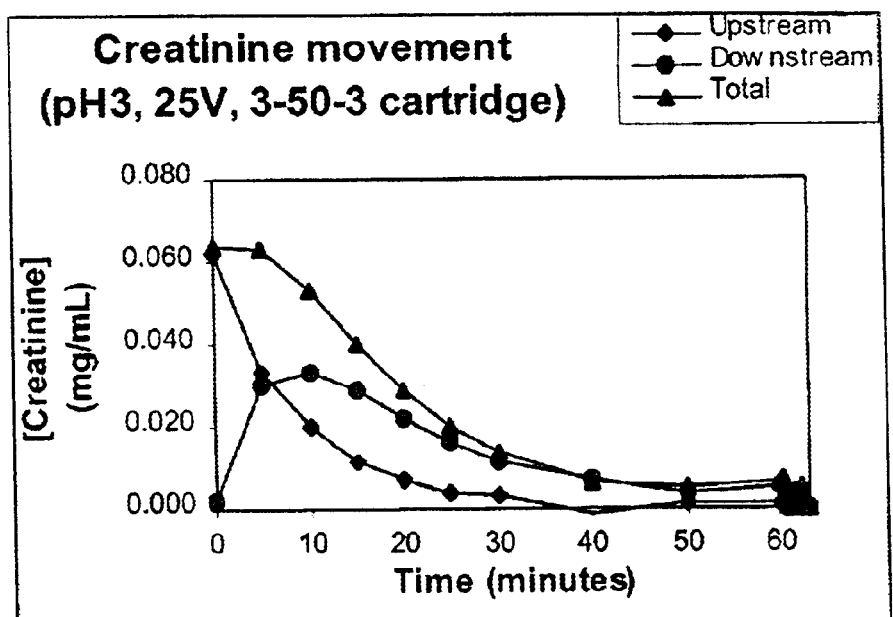
FIG. 6. Creatinine was rapidly removed from the upstream of the GradiFlow™ instrument at 25V. Creatinine entered the downstream of the GradiFlow™, but was not retained by the 3 kDa restriction membrane, so the downstream concentration was also rapidly depleted.

FIG. 6 shows that Creatinine was rapidly removed from the upstream of the GradiFlow™ instrument at 25V. Creatinine entered the downstream of the GradiFlow™, but was not retained by the 3 kDa restriction membrane, so the downstream concentration was also rapidly depleted.

Factors Affecting Creatinine Removal in the GradiFlow Method

Creatinine was dissolved in an appropriate buffer and placed in the sample stream of a GradiFlow™ device, with the GradiFlow™ cartridge constructed in dialysis configuration. The circulating buffer stream was selected to match the solution in which creatinine had been dissolved. The buffer pH, salt concentration, temperature of the system and applied voltage/current were varied systematically to determine the effect each variable had on the rate of creatinine removal. The creatinine solution was pumped through the GradiFlow™ device at 20 mL/min, with samples generally being taken at 5 minute intervals. The timed samples were then assayed for creatinine content.

The Effect of pH on Creatinine Removal

One hundred Tg/mL Creatinine was dissolved in buffers with pH varying from 3 to 9 and processed through the GradiFlow™ using an electrical potential of 20V. Creatinine has a pK of 10.4 indicating that creatinine is uncharged at pH 10.4, and positively charged at pH conditions lower than this pK value. Creatinine removal was most rapid at pH 3, and was observed to be progressively slower as the buffer pH was raised to 9.

Figure 7:
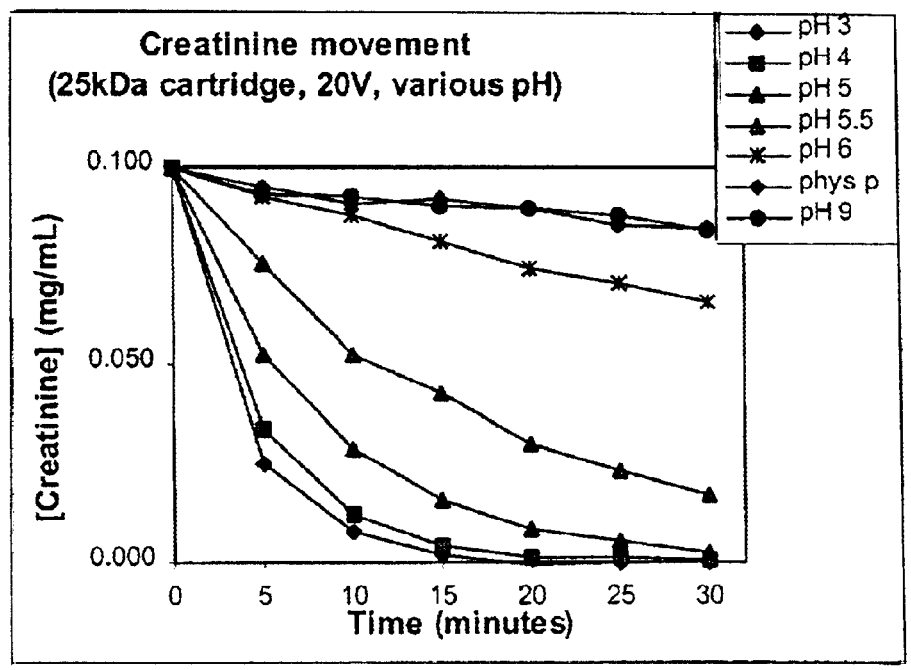
FIG. 7. Creatinine removal is dependent on pH, with lower pH conditions resulting in more rapid removal of creatinine from aqueous solutions.

FIG. 7 shows Creatinine removal is dependent on pH, with lower pH conditions resulting in more rapid removal of creatinine from aqueous solutions.

The of Voltage on Creatinine Removal

One hundred Tg/mL creatinine was dissolved in GABA/acetate buffer, pH 3, and processed in the GradiFlow™ as above. Electrical potentials between 0 and 100 V were applied to the system. The increase in applied voltage accelerated the removal of creatinine from the sample stream.

Figure 8:
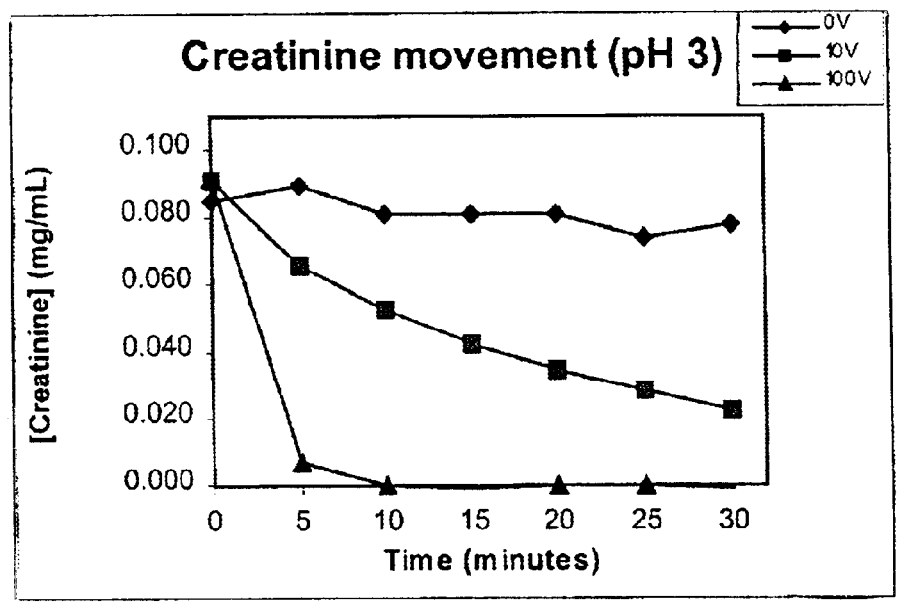
FIG. 8. The application of increasing voltage in the GradiFlow™ system accelerated the removal of creatinine from the sample stream.

FIG. 8 shows the application of increasing voltage in the GradiFlow system accelerated the removal of creatinine from the sample stream.

The Effect of NaCl on the Removal of Creatinine

One hundred Tg/mL creatinine was dissolved in GABA/acetate-buffer, pH 3, with the buffer containing NaCl at concentrations between 0 and 150 mM. The addition of NaCl caused a slight decrease in the rate of creatinine removal, suggesting that the presence of other charge carrying molecules in the solution reduced the level of electrical force available for driving the removal of creatinine.

The Effect of Membrane Molecular Weight Cutoff on Creatinine Removal

One hundred Tg/mL creatinine was dissolved in GABA/acetate buffer, pH 3, and processed in the GradiFlow™ as previously, using membranes with varying molecular weight cutoff values between 3 and 75 kDa. The results generated indicated that the movement of creatinine was influenced by membrane molecular mass cutoff, with the rate of removal of creatinine becoming progressively faster as the membrane pore size was increased.

Figure 9:
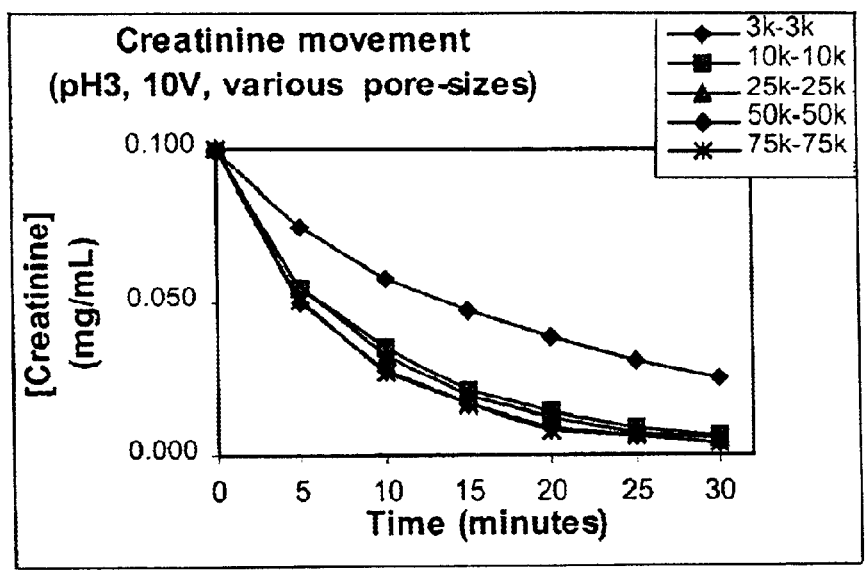
FIG. 9. Increasing the size of the membrane molecular mass cutoff value allowed creatinine removal to proceed at a progressively faster rate.

FIG. 9 shows increasing the size of the membrane molecular mass cutoff value allowed creatinine removal to proceed at a progressively faster rate.

The Effect of Temperature on the Rate of Creatinine Removal

One hundred Tg/mL creatinine was dissolved in GABA/acetate buffer and processed in the GradiFlow™ as above. The circulating GABA/acetate buffer was maintained at temperatures between 4 and 37° C. to examine the effect of temperature on the rate of creatinine removal. It was observed that the rate of creatinine removal increased with increasing buffer temperature.

Removal of Creatinine from Plasma

Figure 10:
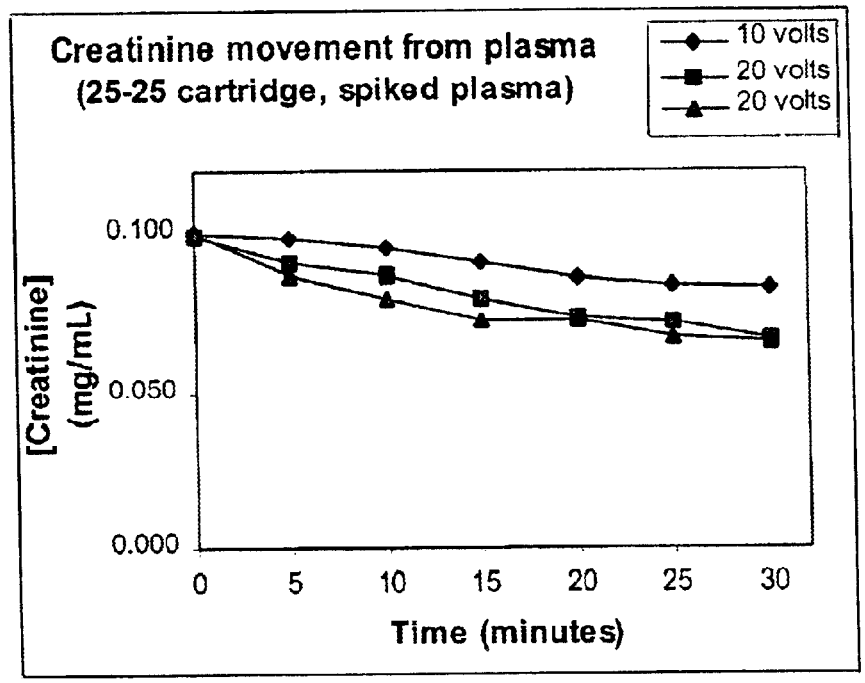
FIG. 10. Creatinine was removed from plasma using 10 and 20V potentials.
Figure 11:
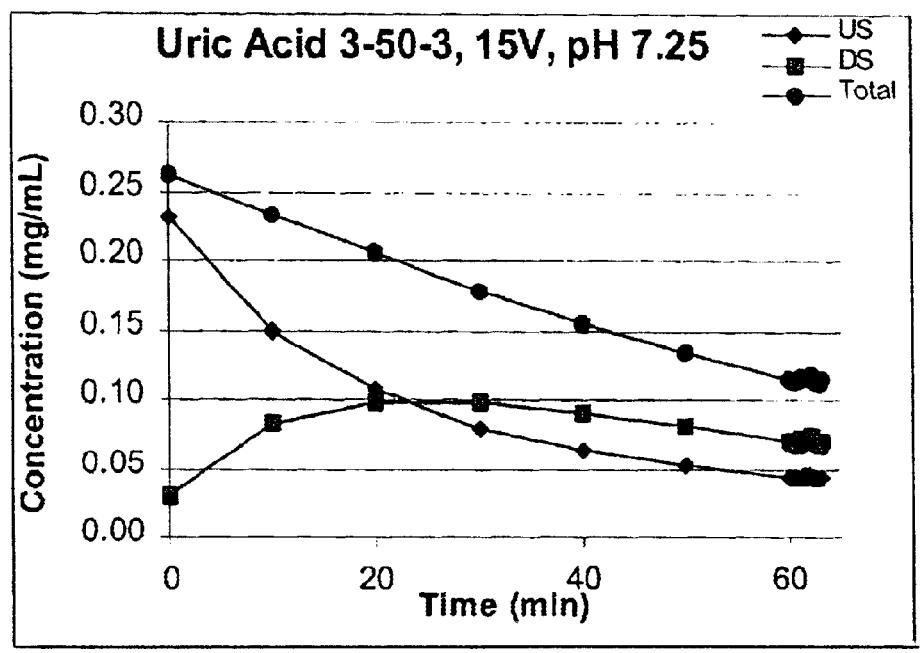
FIG. 11. Uric acid was rapidly removed from the upstream, passing through the downstream to reach the buffer stream.

Normal human plasma was made 100 Tg/mL in creatinine and the plasma processed in the GradiFlow using 10 and 20V potentials. FIG. 10 shows that creatinine was successfully removed from human plasma under these conditions.

Electrically Driven Uric Acid Removal

Demonstration of the Removal or Uric Acid

Three hundred Tg/mL Uric acid was dissolved in Hepes Imidazole buffer, pH 7.26 and placed in the upstream of the GradiFlow™ instrument. Hepes Imidazole buffer, chilled to 4C, was recirculated in the buffer stream of the GradiFlow™ device. The membrane cartridge used included 3 kDa restriction membranes and a 50 kDa separation. membrane. When the GradiFlow™ instrument was run using an electrical potential of 15V, Uric acid was found to be removed from the upstream. The Uric acid was found to accumulate transiently in the downstream, from which it was subsequently removed to the buffer stream.

Factors Affecting the Removal of Uric Acid Method

Uric acid was dissolved in an appropriate buffer and placed in the sample stream of a GradiFlow™ device, with the GradiFlow™ cartridge constructed in dialysis configuration. The circulating buffer stream was selected to match the solution in which uric acid had been dissolved. The membrane pore size, salt concentration, temperature of the system and applied voltage/current were varied systematically to determine the effect each variable had on the rate of uric acid removal. The uric acid solution was pumped through the GradiFlow™ device at 20 mL/min, with samples generally being taken at 5 minute intervals. The timed samples were then assayed for uric acid content.

The Effect of Voltage on Uric Acid Removal

Three hundred Tg/mL Uric acid in Hepes/Imidazole buffer was processed in the GradiFlow™ at using electrical potentials from 0 to 100 V. It was observed the Uric acid removal was faster with increasing voltage.

Figure 12:
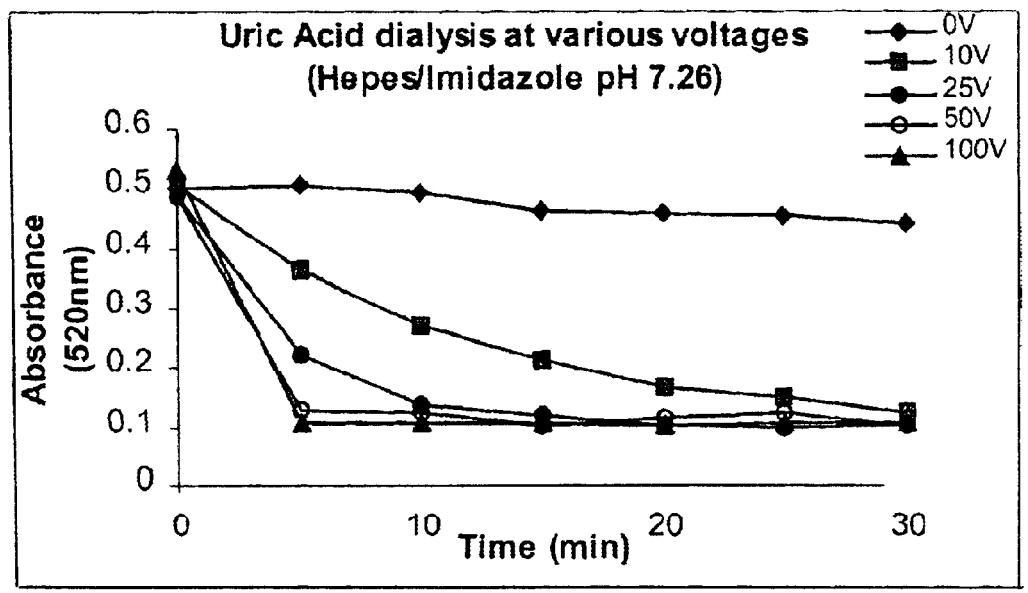
FIG. 12. Increasing voltages resulted in more rapid removal of Uric acid from Hepes/Imidazole buffer.

FIG. 12 shows increasing voltages resulted in more rapid removal of Uric acid from Hepes/Imidazole buffer.

The Effect of Membrane Pore Size on Uric acid Removal

Three hundred Tg/mL Uric acid in Hepes/Imidazole buffer was processed in the GradiFlow™ as above, using an electrical potential of 10V. The molecular weight cutoff of the membranes used in the GradiFlow™ cartridge was carried between 3 and 75 kDa. It was observed that as the molecular mass cutoff value of the membranes was increased, Uric acid was more rapidly cleared from the GradiFlow™ sample stream.

Figure 13:
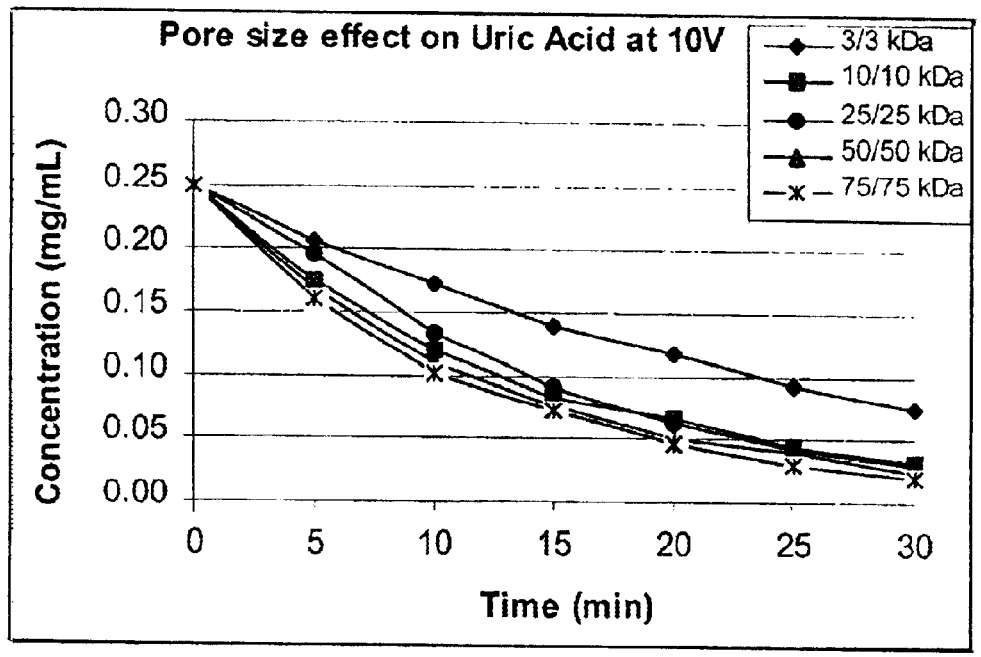
FIG. 13. Increasing the molecular mass cutoff of the GradiFlow™ membranes resulted in more rapid removal of Uric acid from the sample stream.

FIG. 13 shows increasing the molecular mass cutoff of the GradiFlow membranes resulted in more rapid removal of Uric acid from the sample stream.

The Effect of NaCl on Uric on Uric Acid Removal

Three hundred Tg/mL Uric acid in Hepes/Imidazole was processed in the GradiFlow™ using 25 kDa cutoff membranes and an electrical potential of 10V. NaCl was included in the sample and buffer streams at concentrations from 0 to 150 mM. The addition of increasing concentrations of NaCl to the buffer system resulted in a progressive decrease in the rate of uric acid clearance.

Figure 14:
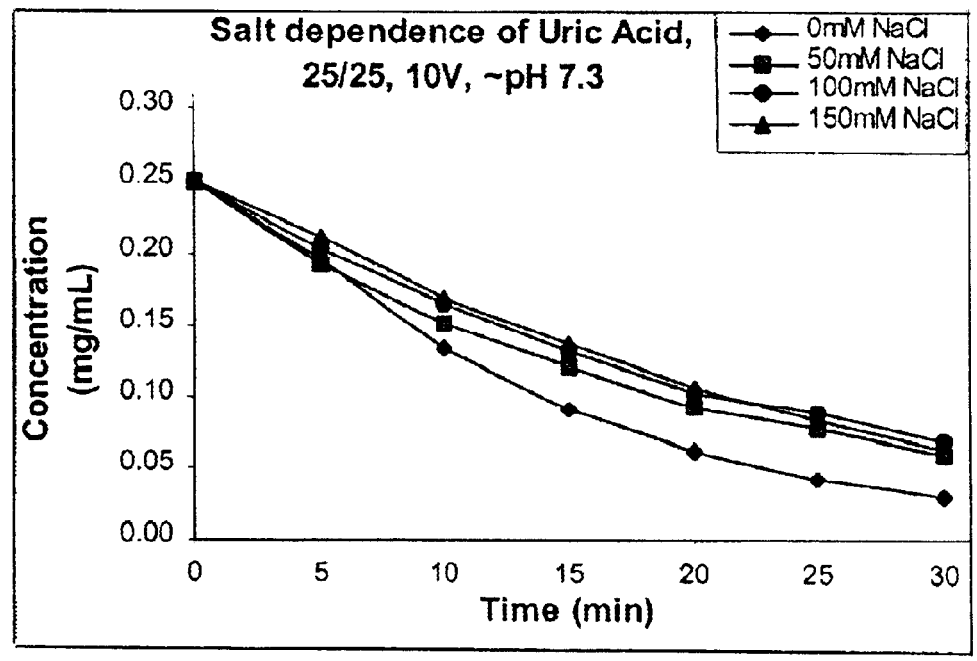
FIG. 14. The addition of NaCl caused a dose-dependent decrease in the rate of uric acid removal.

FIG. 14 shows that the addition of NaCl caused a dose-dependent decrease in the rate of uric acid removal.

The Effect of Temperature on the Rate of Uric Acid Removal

Three hundred Tg/mL Uric acid in Hepes/Imidazole buffer was processed in the GradiFlow™ as above 25 kDa membranes and a 10V. The recirculating buffer was maintained at temperatures between 4 and 37° C. The rate of Uric acid removal was found to increase with increasing temperature.

Figure 15:
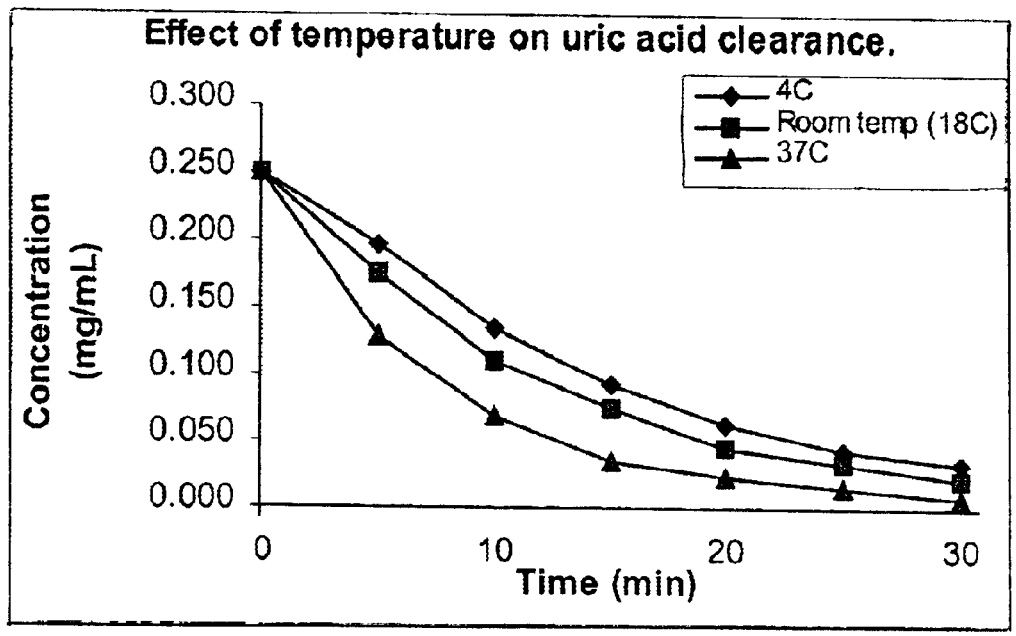
FIG. 15. Increasing buffer temperature resulted in more rapid removal of Uric acid.

FIG. 15 shows that increasing buffer temperature resulted in more rapid removal of Uric acid.

The Removal of Uric Acid from Plasma

Figure 16:
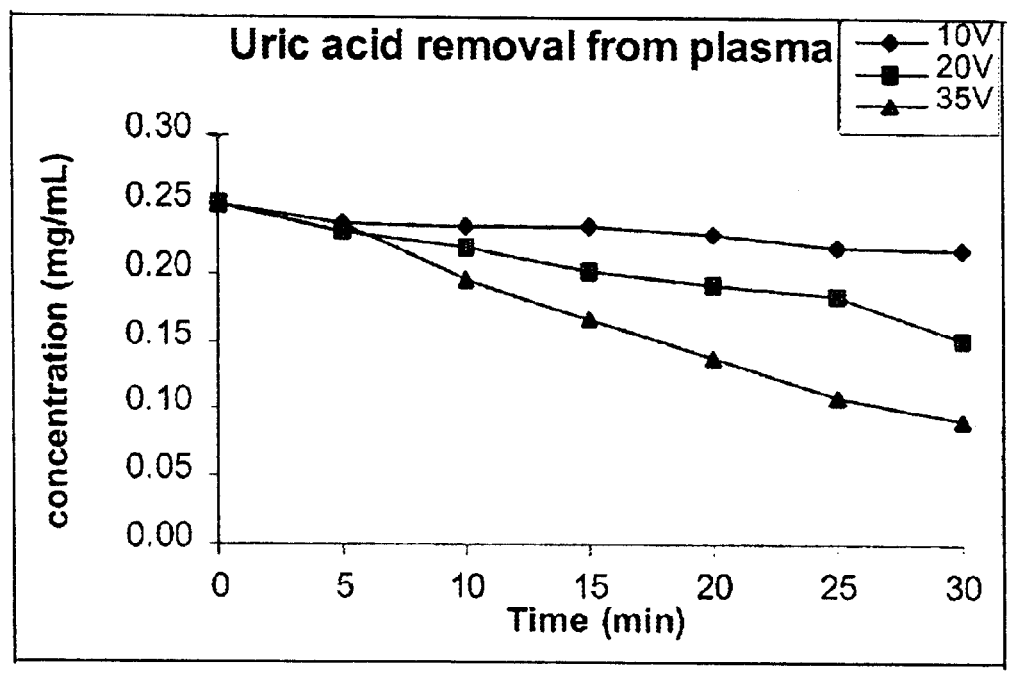
FIG. 16. Uric acid was readily removed from human plasma in a voltage dependent manner.

Normal human plasma was made 300 Tg/mL in Uric acid. The modified plasma was processed in the GradiFlow as previously, using 25 kDa membranes, PBS buffer and using voltages from 10 to 30V. FIG. 16 shows that Uric acid was readily removed from human plasma in a voltage dependent manner.

Electrically Driven Removal of Phosphate Ions

Phosphate removal is one of the key deficiencies in existing renal replacement dialysis technology. The capacity of the GradiFlow™ to rapidly desalt/dialyse aqueous solutions suggested the applicability of the GradiFlow™ technology in the area of rapid phosphate removal from blood. The GradiFlow™ system was found to rapidly remove phosphate ions from both aqueous solutions and plasma.

Demonstration of Phosphate Removal from Aqueous Solution

One hundred Tg/mL sodium phosphate was dissolved in Hepes/Imidazole buffer and placed in the upstream of the GradiFlow™ device. Hepes/Imidazole buffer, pH 7.2 was placed in the downstream and buffer stream of the GradiFlow™ instrument. The membrane cartridge used included 3 kDa restriction membranes and a 10 kDa separation membrane. Electrical potentials from 0 to 50V were applied and the changes in phosphate concentration monitored as a function of time. When a voltage was applied, phosphate in the downstream was also rapidly depleted, the downstream. The quantity of phosphate in the downstream was also rapidly depleted, indicating that the phosphate ions continued to migrate towards the positive electrode, leaving the downstream and entering the recirculating buffer stream. The rate of phosphate removal was also observed to be dependent on the applied voltage.

Figure 17:
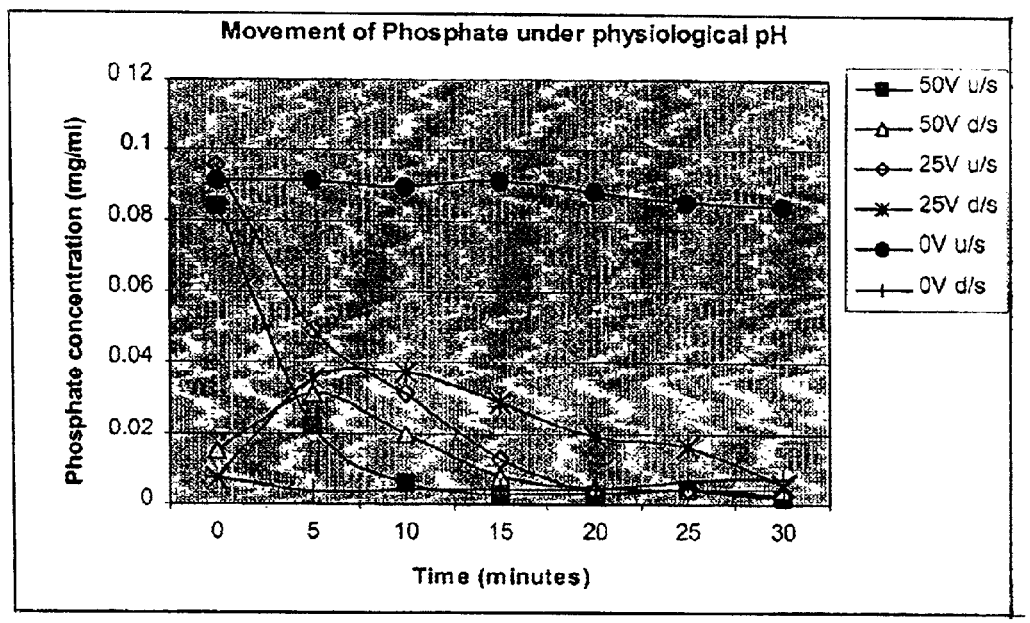
FIG. 17. Phosphate ions were found to migrate from the upstream, through the downstream, into the buffer stream in a voltage dependent manner.

FIG. 17 shows phosphate ions were found to migrate from the upstream, through the downstream, into the buffer stream in a voltage dependent manner.

Removal of Phosphate from Plasma

Figure 18:
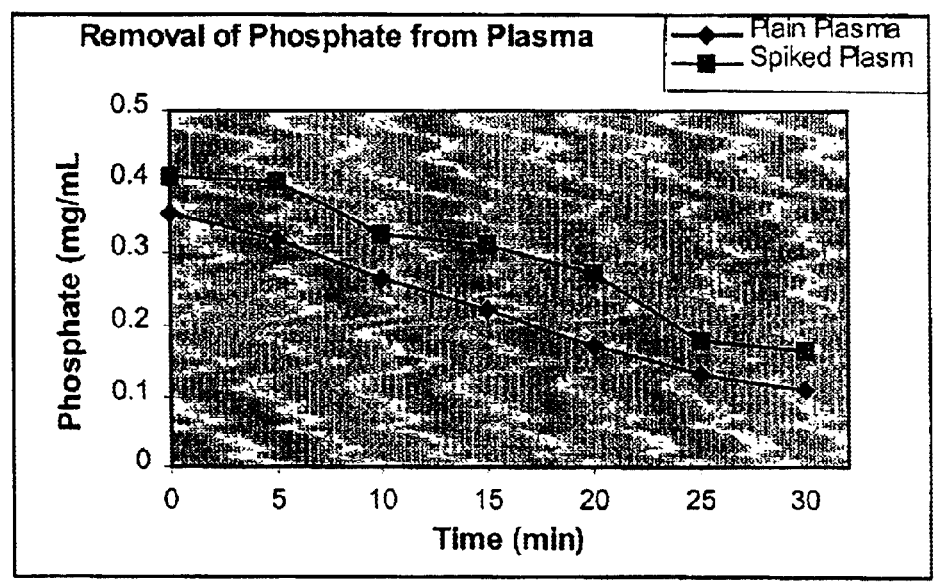
FIG. 18. Phosphate was rapidly removed from plasma using a 50V electric potential.

Unmodified human plasma, or plasma containing an additional 0.1 mg/mL phosphate, was processed in the GradiFlow™. The membrane cartridge was constructed in dialysis configuration using 10 kDa restriction and separation membranes, Hepes/Imidazole buffer, pH 7.2, and an electrical potential of 50V. Samples of the plasma were taken every 5 minutes and assayed for phosphate content. The results shown in FIG. 18 demonstrate the rapid removal of phosphate from human plasma.

Removal of Proteins from Plasma and Whole Blood

General Protein Removal (Using Human Serum Albumin (HSA) As an Example)

Figure 19:
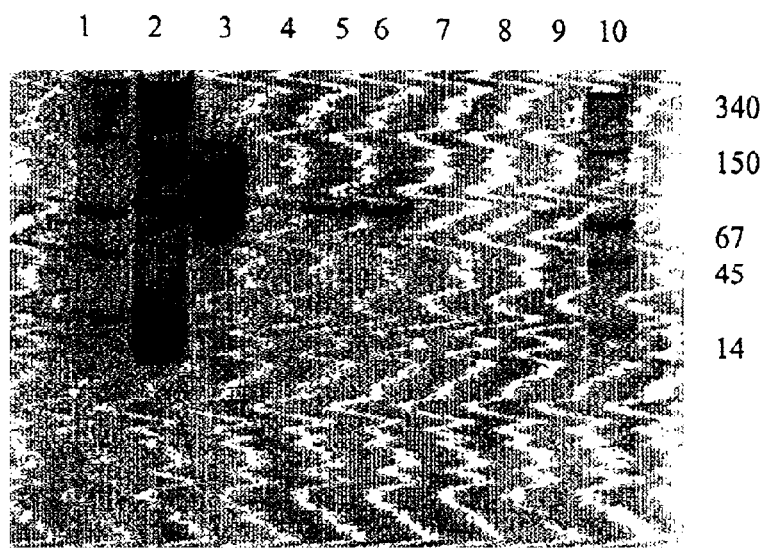
FIG. 19. Native PAGE analysis of proteins removed from whole blood using the GradiFlow™ system. Lanes 1 and 10 are molecular weight markers, with size in kDa shown at the right side. Lane 2 is diluted plasma. Lane 3 is red cell lysate, predominantly haemoglobin. Lane 4 shows albumin and other smaller proteins removed from blood that had been passed through the GradiFlow™ 10 times with an applied voltage of 50V at 4C. Lanes 5 and 6 show proteins removed from blood using 100V at 4C after 5 and 10 passes respectively. Lanes 7,8 and 9 shows proteins removed from whole blood after 10 passes at room temperature, using 0, 50 and 100V respectively.

The ability to eliminate disease related proteins from the circulation of patients relies on the capacity of the GradiFlow™ system to remove proteins from whole blood. Albumin was chosen as a target blood protein to demonstrate the process according to the present invention. In practice, however, proteins like autoantibodies (typically IgG or IgM classes) will be targeted for removal from blood or plasma. To demonstrate this phenomenon, whole blood was circulated in the upstream of a GradiFlow™ device, with PBS buffer placed in the downstream and in the recirculating buffer tank, which was maintained at either 4° C. or room temperature. Either 50 or 100V potential was applied in the GradiFlow™ system. Samples of the downstream were collected and analysed by native PAGE on a 4–20% polyacrylamide gel. FIG. 19 shows that albumin (the most abundant protein in blood) is readily removed after passing a volume blood through the GradiFlow™, and that the quantity of protein removed appears to be dependent on the temperature and voltage applied in the GradiFlow™ system.

Removal of Beta-2 Microglobulin

Beta-2 Microglobulin is a normal component of MHC Class I molecules, which are found on the surface of all nucleated cells. This protein is frequently released in to the blood circulation during episodes of immunological activity, such as infections. Normal plasma contains very low concentrations of beta-2 microglobulin, in the order of 3 Tg/mL. This concentration is raised in renal dialysis patients, firstly due to the increased frequency of infections experienced when on dialysis, and secondly due to the poor capacity of conventional renal dialysis technology to remove this protein. As a result of the inability of conventional renal replacement therapy to remove beta-2 microglobulin, the concentration of this protein increases in the blood circulation of renal dialysis patients. The primary consequence of this accumulation of beta-2 microglobulin is the development of beta-2 microglobulin amyloid fibrils in the bones and other tissues of renal dialysis patients, which affects bone structure and bone marrow function.

Figure 20:
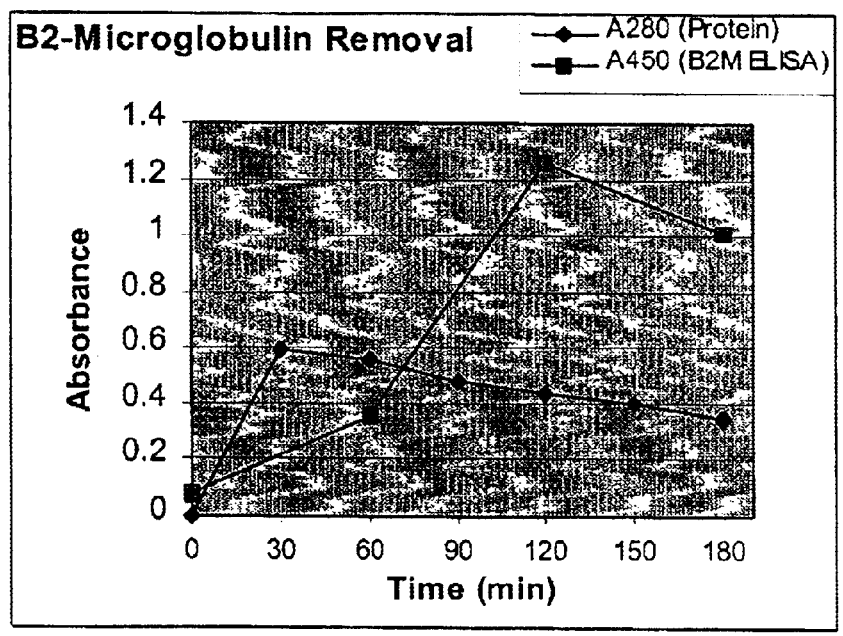
FIG. 20. The accumulation of protein removed from plasma. The triangles indicate the A280 (total protein absorbance) in the downstream. The squares indicate the relative amount of beta-2 microglobulin in the downstream.

The present inventors have tested the ability of the GradiFlow™ to remove beta-2 microglobulin from normal human plasma. Forty mL of plasma was diluted 1:1 in Tris/borate buffer pH 9 and processed in the GradiFlow™ using 3 kDa restriction membranes and 25 kDa separation membranes. A maximum potential of 250V was applied to the system, with the circulation buffer maintained at 4C. The absorbance at 280 nm of the downstream was measured at 30 minute intervals, and the beta-2 microglobulin content of the downstream was determined by and ELISA method in samples taken every hour. The ELISA method employed a rabbit polyclonal antiserum specific to detect beta-2 microglobulin specifically. FIG. 20 shows that low molecular weight proteins were rapidly removed from plasma, and that beta-2 microglobulin was detectable in the downstream. The gradual reduction in total protein in the downstream (A280 points) may relate to the gradual electrophorsis of very small proteins and peptides through the 3 kDa restriction membranes or the adhesion of proteins to the restriction membranes.

SUMMARY

Urea removal has been shown to be independent of voltage, current, pH and salt concentration. Urea removal has been shown to be dependent on temperature, membrane molecular weight cutoff and the starting concentration of urea. Urea removal from plasma has been demonstrated. Urea, being an uncharged molecule, does not move in response to electrical field variations, rather its movement is due entirely to passive diffusion phenomena. The ability of the GradiFlow™ system to remove Urea is of significance to the GradiFlow™ renal dialysis application, as urea is the mayor nitrogenous waste that must be removed. This is also first demonstration of passive diffusion phenomena in the GradiFlow™ system, indicating the GradiFlow™ may be used for the removal and/or purification of uncharged solutes while simultaneously removing charged molecules by electrophoretic means.

Creatinine is a charged nitrogenous waste material which has been shown to be removed from plasma, and whose rate of removal has been shown to be dependent on voltage, pH, salt concentration, temperature and membrane pore size. The capacity of the GradiFlow™ system to rapidly remove charged nitrogenous wastes is significant to the GradiFlow™ capacity in renal dialysis.

Uric acid was removed from aqueous solutions and from plasma. Removal of Uric acid was shown to be dependent on voltage, membrane pore size, temperature and salt concentration. Uric acid removal is another example of electrically driven dialysis which allows rapid removal of nitrogenous wastes from plasma.

The removal of phosphate ions from blood and plasma is a critical application of GradiFlow™ technology to the field of renal dialysis. The inability of current dialysis technologies to remove phosphate ions is an area that could be readily addressed by a variation of the GradiFlow™ technology using electrically driven dialysis to remove charged solutes. The general principle of removing charged ions which is demonstrated here van also be considered to apply to other salt ions such as sodium, potassium, chloride and so on. The removal of excess concentration of these ions would also be made more rapid using electrically driven dialysis systems.

The demonstration of the ability of GradiFlow™ technology to remove proteins, specifically albumin and beta-2 microglobulin, from whole blood and plasma implies that, using the correct conditions of membrane molecular weight cutoff, voltage and buffer solution, individual disease related proteins may be removed from blood or plasma for therapeutic purposes. This potential should not be restricted to the two proteins for which the principle has been demonstrated. In theory, any protein for which a specific combination of electrical field and membrane selectivity can be specified, could be removed from blood or plasma for therapeutic purposes.

CONCLUSIONS

It is apparent from the data presented that the GradiFlow™ system is useful for the removal of nitrogenous wastes, phosphate ions, and proteins such as albumin and beta-2 microglobulin, from aqueous solutions, plasma and blood. The ability to remove waste or unwanted materials from blood or plasma by the simultaneous use of diffusive and electrophoretic principles in a single cartridge system is an advantage. For example, urea can be removed on the basis of latent diffusion while other waste materials can be removed on the basis of charge during the same process. The capacity of the basic GradiFlow™ system to perform these functions indicates the potential applications of the GradiFlow™ system in the field of renal dialysis and other blood purification applications which require the selective removal of proteins and other charged or uncharged species from circulating blood or plasma. Modified versions of the GradiFlow™ device can be constructed which could be used either as a complete renal dialysis device, addressing all renal replacement therapy needs including removal of salts, phosphate, nitrogenous wastes, excess water balancing blood pH and removing beta-2 microglobulin. Alternatively, a simpler device may be constructed to function as an addition to existing renal dialysis systems, whose function is to address the deficiencies of the existing systems, i.e., the removal of phosphate and beta-2 microglobulin from either blood or plasma. The present inventors have demonstrated that the Gradiflow™ system is capable of removing all these solutes and proteins. The correct combination of membrane chemistry, dialysis solution, voltage and current conditions, cartridge and tubing materials, pump design etc are all integral to the functioning of the system.

Furthermore, given that individual proteins may be removed from blood and/or plasma, it will be feasible to construct a version of the GradiFlow™ which is designed to selectively remove proteins such as autoantibodies, which may be related to autoimmune diseases such as rheumatoid arthritis, lupus and so on, as well as other proteins which may be causative factors in other diseases. Examples of other proteins or blood contaminants may include the removal of bacterial endotoxins or specific lipoproteins from blood or plasma as a therapeutic measures for treating septic shock or lipid metabolism disorders respectively.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for selectively removing metabolic contaminants from at least one blood component, comprising:
   (a) selecting a first selective membrane composed of a polyacrylamide hydrogel;
   (b) directing a first solvent stream having a selected pH and including at least a metabolic contaminant capable of obtaining a charge and at least one blood component, so as to flow along the first selective membrane, wherein such pH produces a net charge on the metabolic contaminant;
   (c) directing a second solvent stream along the first selective membrane so as to be isolated from the first solvent stream thereby;
   (d) applying at least one voltage potential across each of the first and second solvent streams, the pressure in both streams being substantially equal, wherein the application of such voltage potential causes movement of at least a portion of the charged metabolic contaminants through the first selective membrane into the second solvent stream while at least a portion of the at least one blood component is prevented from entering the second solvent stream wherein substantially all transmembrane migration of the charged metabolic contaminant is initiated by the voltage potential; and (e) maintaining step (d) until the first solvent stream contains the desired purity of the at least one blood component.

2. The method according to claim 1 further wherein at least a portion of uncharged metabolic contaminants contained in the first solvent stream migrate through the selective membrane into the second solvent stream.

3. The method according to claim 2 further comprising placing the at least one blood component from a subject into the first solvent stream.

4. The method according to claim 2 wherein the metabolic contaminants are selected from the group consisting of urea, creatinine, uric acid, phosphate ions, beta-2-microglobulin, autoantibodies, other proteins, and combinations thereof.

5. The method according to claim 2 wherein the separation membrane has a molecular mass cut-off of at least about 3 kDa.

6. The method according to claim 1 further comprising directing a third solvent stream separated from a selected one of the first and second solvent streams by a second selective membrane and applying concurrently the voltage potential across the third solvent stream so as to cause the migration of at a portion of a the charged metabolic contaminants through the second selective membrane and into the third solvent stream.

7. The method according to claim 6 further comprising directing a fourth solvent stream separated from the other of the first and second solvent streams by a third selective membrane and applying concurrently the voltage potential across the fourth solvent stream so as to cause the migration of at least a portion of the charged metabolic contaminants through the third selective membrane and into the fourth solvent stream.

8. A method for selectively removing metabolic contaminants from at least one blood component, comprising:

(a) directing a first solvent stream having a selected pH and including at least a metabolic contaminant capable of obtaining a charge and at least one blood component, so as to flow along a first selective membrane, wherein such pH produces a net charge on the metabolic contaminant;

(b) directing a second solvent stream along the first selective membrane so as to be isolated from the first solvent stream thereby;

(c) applying at least one voltage potential across each of the first and second solvent streams, whereby the application of such voltage potential moves at least a portion of the charged metabolic contaminants through the first selective membrane into the second solvent stream while at least a portion of the at least one blood component is prevented from entering the second solvent stream, whereby substantially all transmembrane migration of the charged metabolic contaminant is initiated by the voltage potential;

(d) periodically stopping and reversing the voltage potential to cause movement of at least any of the at least one blood component having entered the first selective membrane to move back into the first solvent stream and wherein substantially not causing any of the metabolic contaminants that have entered the second solvent stream to re-enter the first solvent stream; and (e) maintaining steps (c) or (d) until the first solvent stream contains the desired purity of the at least one blood component.

9. A method for selectively removing metabolic contaminants from at least one blood component, comprising:

(a) placing at least one blood component from a subject into a first solvent stream;

(b) directing a first solvent stream having a selected pH and including at least a metabolic contaminant capable of obtaining a charge and at least one blood component, so as to flow along a first selective membrane, wherein such pH produces a net charge on the metabolic contaminant;

(c) directing a second solvent stream along the first selective membrane so as be isolated from the first solvent stream thereby;

(d) applying at least one voltage potential across each of the first and second solvent streams, whereby the application of such voltage potential moves at least a portion of the charged metabolic contaminants through the first selective membrane into the second solvent stream while at least a portion of the at least one blood component is prevented from entering the second solvent stream, whereby substantially all transmembrane migration of the charged metabolic contaminant is initiated by the voltage potential;

(e) maintaining step (d) until the first solvent stream contains the desired purity of the at least one blood component; and (f) returning at least one blood component in the first solvent stream to the subject.

10. The method according to claim 9 wherein the at least one blood component is recirculated between the subject and the first solvent stream.

11. A method for selectively removing metabolic contaminants from at least one blood component, comprising:

(a) directing a first solvent stream having a selected pH and including at least a metabolic contaminant capable of obtaining a charge and at least one blood component, so as to flow along a first selective membrane, wherein such pH produces a net charge on the metabolic contaminant, and at least one blood component has undergone treatment consisting of diffusive hemodialysis, convective hemodialysis, hemofiltration, hemodialfiltration, and combinations thereof prior to, subsequent to, or concurrently therewith step (a);

(b) directing a second solvent stream along the first selective membrane so as be isolated from the first solvent stream thereby;

(c) applying at least one voltage potential across each of the first and second solvent streams, whereby the application of such voltage potential moves at least a portion of the charged metabolic contaminants through the first selective membrane into the second solvent stream while at least a portion of the at least one blood component is prevented from entering the second solvent stream, whereby substantially all transmembrane migration of the charged metabolic contaminant is initiated by the voltage potential; and (d) maintaining step (c) until the first solvent stream contains the desired purity of the at least one blood component.

12. A method for selectively removing metabolic contaminants from at least one blood component, comprising:
(a) selecting a first selective membrane composed of a polyacrylamide hydrogel;
(b) directing a first solvent stream having a selected pH and including at least a metabolic contaminant capable of obtaining a charge, an uncharged metabolic contaminant, and at least one blood component, so as to flow along the first selective membrane, wherein such pH produces a net charge on the metabolic contaminant capable of obtaining a charge;
(c) directing a second solvent stream along the first selective membrane so as to be isolated from the first solvent stream thereby;
(d) applying at least one voltage potential across each of the first and second solvent streams, the pressure in both streams being substantially equal, wherein the application of such voltage potential causes movement of at least a portion of the charged metabolic contaminants through the first selective membrane into the second solvent stream while at least a portion of the at least one blood component is prevented from entering the second solvent stream wherein substantially all transmembrane migration of the charged metabolic contaminants is initiated by the voltage potential, wherein at least a portion of the uncharged metabolic contaminants contained in the first solvent stream migrates through the selective membrane into the second solvent stream; and
(e) maintaining step (d) until the first solvent stream contains the desired purity of the at least one blood component.

13. The method according to claim 12 further comprising directing a third solvent stream separated from a selected one of the first and second solvent streams by a second selective membrane and applying concurrently the voltage potential across the third solvent stream so as to cause the migration of at least a portion of a the charged metabolic contaminants through the second selective membrane and into the third solvent stream.

14. The method according to claim 13 further comprising directing a fourth solvent stream separated from the other of the first and second solvent streams by a third selective membrane and applying concurrently the voltage potential across the fourth solvent stream so as to cause the migration of at least a portion of the charged metabolic contaminants through the third selective membrane and into the fourth solvent stream.

15. The method according to claim 12 further comprising placing at least one blood component from a subject into the first solvent stream.

16. The method according to claim 12 wherein the metabolic contaminants are selected from the group consisting of urea, creatinine, uric acid, phosphate ions, beta-2-microglobulins, autoantibodies, other proteins, and combinations thereof.

17. The method according to claim 12 wherein the selective membrane has a molecular mass cut-off of at least about 3 kDa.

18. A method for selectively removing metabolic contaminants from at least one blood component, comprising:
(a) directing a first solvent stream having a selected pH and including at least a metabolic contaminant capable of obtaining a charge, an uncharged metabolic contaminant, and at least one blood component, so as to flow along a first selective membrane, wherein such pH produces a net charge on the metabolic contaminant capable of obtaining a charge;
(b) directing a second solvent stream along the first selective membrane so as to be isolated from the first solvent stream thereby;
(c) applying at least one voltage potential across each of the first and second solvent streams, wherein the application of such voltage potential causes movement of at least a portion of the charged metabolic contaminants through the first selective membrane into the second solvent stream while at least a portion of the at least one blood component is prevented from entering the second solvent stream wherein substantially all transmembrane migration of the charged metabolic contaminants is initiated by the voltage potential, wherein at least a portion of the uncharged metabolic contaminants contained in the first solvent stream migrates through the selective membrane into the second solvent stream; and
(d) periodically stopping and reversing the voltage potential to cause movement of at least any of the at least one blood component having entered the first selective membrane to move back into the first solvent stream and wherein substantially not causing any of the metabolic contaminants that have entered the second solvent stream to re-enter the first solvent stream; and
(e) maintaining steps (c) or (d) until the first solvent stream contains the desired purity of the at least one blood component.

19. A method for selectively removing metabolic contaminants from at least one blood component, comprising:
(a) placing at least one blood component from a subject into a first solvent stream;
(b) directing the first solvent stream having a selected pH and including at least a metabolic contaminant capable of obtaining a charge, an uncharged metabolic contaminant, and at least one blood component, so as to flow along a first selective membrane, wherein such pH produces a net charge on the metabolic contaminant capable of obtaining a charge;
(c) directing a second solvent stream along the first selective membrane so as to be isolated from the first solvent stream thereby;
(d) applying at least one voltage potential across each of the first and second solvent streams, wherein the application of such voltage potential causes movement of at least a portion of the charged metabolic contaminants through the first selective membrane into the second solvent stream while at least a portion of the at least one blood component is prevented from entering the second solvent stream wherein substantially all transmembrane migration of the charged metabolic contaminants is initiated by the voltage potential, wherein at least a portion of the uncharged metabolic contaminants contained in the first solvent stream migrates through the selective membrane into the second solvent stream;
(e) maintaining step (d) until the first solvent stream contains the desired purity of the at least one blood component; and
(f) returning at least one blood component in the first solvent stream to the subject.

20. The method according to claim 19 wherein the at least one blood component is recirculated between the subject and the first solvent stream.

21. A method for selectively removing metabolic contaminants from at least one blood component, comprising:

(a) placing at least one blood component from a subject into a first solvent stream, wherein at least one blood component has undergone treatment consisting of diffusive hemodialysis, convective hemodialysis, hemofiltration, hemodialfiltration, and combinations thereof prior to, subsequent to, or concurrently therewith step (a);

(b) directing the first solvent stream having a selected pH and including at least a metabolic contaminant capable of obtaining a charge, an uncharged metabolic contaminant, and at least one blood component, so as to flow along a first selective membrane, wherein such pH produces a net charge on the metabolic contaminant capable of obtaining a charge;

(c) directing a second solvent stream along the first selective membrane so as to be isolated from the first solvent stream thereby;

(d) applying at least one voltage potential across each of the first and second solvent streams, wherein the application of such voltage potential causes movement of at least a portion of the charged metabolic contaminants through the first selective membrane into the second solvent stream while at least a portion of the at least one blood component is prevented from entering the second solvent stream wherein substantially all transmembrane migration of the charged metabolic contaminants is initiated by the voltage potential, wherein at least a portion of the uncharged metabolic contaminants contained in the first solvent stream migrates through the selective membrane into the second solvent stream; and (e) maintaining step (d) until the first solvent stream contains the desired purity of the at least one blood component.

22. A method for selectively removing metabolic contaminants from at least one blood component, comprising:

(a) selecting a first selective membrane composed of a polyacrylamide hydrogel;

(b) directing a first solvent stream having a selected pH and including at least a metabolic contaminant and at least one blood component so as to flow along the first selective membrane;

(c) directing a second solvent stream along the first selective membrane so as to be isolated from the first solvent stream thereby;

(d) applying at least one voltage potential across each of the first and second solvent streams, the pressure in both streams being substantially equal, wherein the application of such voltage potential causes movement of at least a portion of the at least one blood component through the first selective membrane into the second solvent stream while at least a portion of the metabolic contaminants is prevented from entering the second solvent stream wherein substantially all transmembrane migration of the at least one blood component is initiated by the voltage potential; and (e) maintaining step (d) until the second solvent stream contains the desired purity of the at least one blood component.

23. The method according to claim 22 further comprising directing a third solvent stream separated from a selected one of the first and second solvent streams by a second selective membrane and applying concurrently the voltage potential across the third solvent stream so as to cause the migration of at least a portion of at least one of the at least one blood component and any metabolic contaminants through the second selective membrane and into the third solvent stream.

24. The method according to claim 23 further comprising directing a fourth solvent stream separated from the other of the first and second solvent streams by a third selective membrane and applying concurrently the voltage potential across the fourth solvent stream so as to cause the migration of at least a portion of at least one of the at least one blood component and metabolic contaminants through the third selective membrane and into the fourth solvent stream.

25. The method according to claim 22 further comprising placing the at least one blood component from a subject into the first solvent stream.

26. The method according to claim 22 wherein the metabolic contaminants are selected from the group consisting of urea, creatinine, uric acid, phosphate ions, beta-2-microglobulins, autoantibodies, and other proteins, and combinations thereof.

27. The method according to claim 22 wherein the selective membrane has a molecular mass cut-off at least about 3 kDa.

28. A method for selectively removing metabolic contaminants from at least one blood component, comprising:

(a) directing a first solvent stream having a selected pH and including at least a metabolic contaminant and at least one blood component so as to flow along a first selective membrane;

(b) directing a second solvent stream along the first selective membrane so as to be isolated from the first solvent stream thereby;

(c) applying at least one voltage potential across each of the first and second solvent streams, wherein the application of such voltage potential causes movement of at least a portion of the at least one blood component through the first selective membrane into the second solvent stream while at least a portion of the metabolic contaminants is prevented from entering the second solvent stream wherein substantially all transmembrane migration of the least one blood component is initiated by the voltage potential;

(d) periodically stopping and reversing the voltage potential to cause movement of at least any of the metabolic contaminants having entered the first selective membrane to move back into the first solvent stream and wherein substantially not causing any of the at least one blood component that has entered the second solvent stream to re-enter the first solvent stream; and (e) maintaining steps (c) or (d) until the second solvent stream contains the desired purity of the at least one blood component.

29. A method for selectively removing metabolic contaminants from at least one blood component, comprising:

(a) placing at least one blood component form a subject into a first solvent stream;

(b) directing the first solvent stream having a selected pH and including at least a metabolic contaminant and at least one blood component so as to flow along a first selective membrane;

(c) directing a second solvent stream along the first selective membrane so as to be isolated from the first solvent stream thereby;

(d) applying at least one voltage potential across each of the first and second solvent streams, wherein the application of such voltage potential causes movement of at least a portion of the at least one blood component through the first selective membrane into the second solvent stream while at least a portion of the metabolic contaminants is prevented from entering the second solvent stream wherein substantially all transmembrane migration of the at least one blood component is initiated by the voltage potential;

(e) maintaining step (d) until the second solvent stream contains the desired purity of the at least one blood component; and (f) returning at least one blood component in the second solvent stream to the subject.

30. The method according to claim 29 wherein the at least one blood component is recirculated between the subject and the first solvent stream.

31. A method for selectively removing metabolic contaminants from at least one blood component, comprising:

(a) directing a first solvent stream having a selected pH and including at least a metabolic contaminant and at least one blood component so as to flow along a first selective membrane, wherein at least one blood component has undergone treatment consisting of diffusive hemodialysis, convective hemodialysis, hemofiltration, hemodialfiltration, and combinations thereof prior to, subsequent to, or concurrently therewith step (a);

(b) directing a second solvent stream along the first selective membrane so as to be isolated from the first solvent stream thereby;

(c) applying at least one voltage potential across each of the first and second, solvent streams, wherein the application of such voltage potential causes movement of at least a portion of the at least one blood component through the first selective membrane into the second solvent stream while at least a portion of the metabolic contaminants is prevented from entering the second solvent stream wherein substantially all transmembrane migration of the least one blood component is initiated by the voltage potential; and (d) maintaining step (c) until the second solvent stream contains the desired purity of at least one blood component.

32. A method for selectively removing selected compounds from at least one blood component, comprising:

(a) selecting a first selective membrane composed of a polyacrylamide hydrogel;

(b) directing a first solvent stream having a selected pH and including at least a selected compound capable of obtaining a charge and at least one blood component, so as to flow along the first selective membrane, wherein such pH produces a net charge on the metabolic contaminant;

(c) directing a second solvent stream along the first selective membrane so as to be isolated from the first solvent stream thereby;

(d) applying at least one voltage potential across each of the first and second solvent streams, the pressure in both streams being substantially equal, wherein the application of such voltage potential causes movement of at least a portion of the selected charged compounds through the first selective membrane into the second solvent stream while at least a portion of the at least one blood component is prevented from entering the second solvent stream wherein substantially all transmembrane migration of the charged compound is initiated by the voltage potential; and (e) maintaining step (d) until the first solvent stream contains the desired purity of the at least one blood component.

33. The method according to claim 32 further wherein at least a portion of selected uncharged compounds contained in the first solvent stream migrate through the selective membrane into the second solvent stream.

34. A method for selectively removing selected compounds from at least one blood component, comprising:

(a) placing at least one blood component from a subject into a first solvent stream;

(b) directing the first solvent stream having a selected pH and including at least a selected compound capable of obtaining a charge and at lease one blood component, so as to flow along a first selective membrane, wherein such pH produces a net charge on the metabolic contaminant;

(c) directing a second solvent stream along the first selective membrane so as to be isolated from the first solvent stream thereby;

(d) applying at least one voltage potential across each of the first and second solvent streams, wherein the application of such voltage potential causes movement of at least a portion of the selected charged compounds through the first selective membrane into the second solvent stream while at least a portion of the at least one blood component is prevented from entering the second solvent stream wherein substantially all transmembrane migration of the charged compound is initiated by the voltage potential;

(e) maintaining step (d) until the first solvent stream contains the desired purity of the at least one blood component; and (f) returning at least one blood component in the first solvent stream to the subject.

35. A method for selectively removing selected compounds from at least one blood component, comprising:

(a) selecting a first selective membrane composed of a polyacrylamide hydrogel;

(b) directing a first solvent stream having a selected pH and including at least a selected compound capable of obtaining a charge, a selected uncharged compounds, and at least one blood component, so as to flow along the first selective membrane, wherein such pH produces a net charge on the selected compound capable of obtaining a charge;

(c) directing a second solvent stream along the first selective membrane so as to be isolated from the first solvent stream thereby;

(d) applying at least one voltage potential across each of the first and second solvent streams, the pressure in both streams being substantially equal, wherein the application of such voltage potential causes movement of at least a portion of the selected charged compounds through the first selective membrane into the second solvent steam while at least a portion of the at least one blood component is prevented from entering the second solvent stream wherein substantially all transmembrane migration of the selected charged compounds is initiated by the voltage potential, wherein at least a portion of the selected uncharged compounds contained in the first solvent stream migrates through the selective membrane into the second solvent stream; and (e) maintaining step (d) until the first solvent stream contains the desired purity of the at least one blood component.

36. A method for selectively removing selected compounds from at least one blood component, comprising:

(a) placing at least one blood component from a subject into a first solvent stream;

(b) directing the first solvent stream having a selected pH and including at least a selected compound capable of obtaining a charge, a selected uncharged compounds, and at least one blood component, so as to flow along a first selective membrane, wherein such pH produces a net charge on the selected compound capable of obtaining a charge;

(c) directing a second solvent stream along the first selective membrane so as to be isolated from the first solvent stream thereby;

(d) applying at least one voltage potential across each of the first and second solvent streams, wherein the application of such voltage potential causes movement of at least a portion of the selected charged compounds through the first selective membrane into the second solvent stream while at least a portion of the at least one blood component is prevented from entering the second solvent stream wherein substantially all transmembrane migration of the selected charged compounds is initiated by the voltage potential, wherein at least a portion of the selected uncharged compounds contained in the first solvent stream migrates through the selective membrane into the second solvent stream;

(e) maintaining step (d) until the first solvent stream contains the desired purity of the at least one blood component; and (f) returning at least one blood component in the second solvent stream to the subject.

37. A method for selectively removing selected compounds from at least one blood component, comprising:

(a) selecting a first selective membrane composed of a polyacrylamide hydrogel;

(b) directing a first solvent stream having a selected pH and including at least a selected compound and at least one blood component so as to flow along the first selective membrane;

(b) directing a second solvent stream along the first selective membrane so as to be isolated from the first solvent stream thereby;

(c) applying at least one voltage potential across each of the first and second solvent streams, the pressure in both streams being substantially equal, wherein the application of such voltage potential causes movement of at least a portion of the at least one blood component through the first selective membrane into the second solvent stream while at least a portion of the selected compounds is prevented from entering the second solvent stream wherein substantially all transmembrane migration of the at least one blood component is initiated by voltage potential; and (d) maintaining step (c) until the second solvent stream contains the desired purity of the at least one blood component.

38. A method for selectively removing selected compounds from at least one blood component, comprising:

(a) placing at least one blood component from a subject into a first solvent stream;

(b) directing the first solvent stream having a selected pH and including at least a selected compound and at least one blood component so as to flow along a first selective membrane;

(c) directing a second solvent stream along the first selective membrane so as to be isolated from the first solvent stream thereby;

(d) applying at least one voltage potential across each of the first and second solvent streams, wherein the application of such voltage potential causes movement of at least a portion of the at least one blood component through the first selective membrane into the second solvent stream while at least a portion of the selected compounds is prevented from entering the second solvent stream wherein substantially all transmembrane migration of the at least one blood component is initiated by the voltage potential; and (e) maintaining step (d) until the second solvent stream contains the desired purity of the at least one blood component; and (f) returning at least one blood component in the second solvent stream to the subject.

39. A method for selectively removing selected compounds from at least one blood component, comprising:

(a) selecting a first selective membrane composed of a polyacrylamide hydrogel;

(b) directing a first solvent stream having a selected pH and including at least a selected compound and at least one blood component so as to flow along the first selective membrane;

(c) directing a second solvent stream along the first selective membrane so as to be isolated from the first solvent stream thereby, the pressure in both streams being substantially equal;

(d) causing migration of at least a portion of the selected charged compounds through the first selective membrane into the second solvent stream while at least a portion of the at least one blood component is prevented from entering the second solvent stream wherein the transmembrane migration of the selected charged compounds is assisted by at least one of an application of a voltage potential across the first and second solvent streams, selected pH of first solvent stream, salt concentration in at least one of first and second solvent streams, concentration of the at least one blood component in the first solvent stream, concentration of the selected compounds in at least one of the first and second solvent streams, temperature of at least one of the first and second solvent streams, and preselected pore size of the selective membrane; and (e) maintaining step (d) until the first solvent stream contains the desired purity of the at least one blood component.

40. A method for selectively removing selected compounds from at least one blood component, comprising:

(a) placing at least one blood component from a subject into a first solvent stream;

(b) directing the first solvent stream having a selected pH and including at least a selected compound and at least one blood component so as to flow along a first selective membrane;

(c) directing a second solvent stream along the first selective membrane so as to be isolated from the first solvent stream thereby;

(d) causing migration of at least a portion of the selected charged compounds through the first selective membrane into the second solvent stream while at least a portion of the at least one blood component is prevented from entering the second solvent stream wherein the transmembrane migration of the selected charged compounds is assisted by at least one of an application of a voltage potential across the first and second solvent streams, selected pH of first solvent stream, salt concentration in at least one of first and second solvent streams, concentration of the at least one blood component in the first solvent stream, concentration of the selected compounds in at least one of the first and second solvent streams, temperature of at least one of the first and second solvent streams, and preselected pore size of the selective membrane;

(e) maintaining step (d) until the first solvent stream contains the desired purity of the at least one blood component; and (f) returning at least one blood component in the first solvent stream to the subject.

41. A method for selectively removing selected compounds from at least one blood component, comprising:

(a) selecting a first selective membrane composed of a polyacrylamide hydrogel;

(b) directing a first solvent stream having a selected pH and including at least a selected compound and at least one blood component so as to flow along a first selective membrane;

(c) directing a second solvent stream along the first selective membrane so as to be isolated from the first solvent stream thereby, the pressure in both streams being substantially equal;

(d) causing migration of at least a portion of the at least one blood component through the first selective membrane into the second solvent stream while at least a portion of the selected compound is prevented from entering the second solvent stream wherein the transmembrane migration of the selected charged compounds is assisted by at least one of an application of a voltage potential across the first and second solvent streams, selected pH of first solvent stream, salt concentration in at least one of first and second solvent streams, concentration of the at least one blood component in the first solvent stream, concentration of the selected compounds in at least one of the first and second solvent streams, temperature of at least one of the first and second solvent streams, and preselected pore size of the selective membrane; and (e) maintaining step (d) until the first solvent stream contains the desired purity of the at least one blood component.

42. A method for selectively removing selected compounds from at least one blood component, comprising:

(a) placing at least one blood component from a subject into a first solvent stream;

(b) directing the first solvent stream having a selected pH and including at least a selected compound and at least one blood component so as to flow along a first selective membrane;

(c) directing a second solvent stream along the first selective membrane so as to be isolated from the first solvent stream thereby;

(d) causing migration of at least a portion of the at least one blood component through the first selective membrane into the second solvent stream while at least a portion of the selected compound is prevented from entering the second solvent stream wherein the transmembrane migration of the selected charged compounds is assisted by at least one of an application of a voltage potential across the first and second solvent streams, selected pH of first solvent stream, salt concentration in at least one of first and second solvent streams, concentration of the at least one blood component in the first solvent stream, concentration of the selected compounds in at least one of the first and second solvent streams, temperature of at least one of the first and second solvent streams, and preselected pore size of the selective membrane;

(e) maintaining step (d) until the first solvent stream contains the desired purity of the at least one blood component; and (f) returning at least one blood component in the second solvent stream to the subject.

* * * * *